US00PP18819P2

(12) United States Plant Patent
Hartman

(10) Patent No.: US PP18,819 P2
(45) Date of Patent: May 20, 2008

(54) ***CALADIUM* PLANT NAMED 'WHITE MARBLE'**

(50) Latin Name: *Caladium ×hortulanum*
Varietal Denomination: White Marble

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 11/648,873

(22) Filed: Dec. 29, 2006

(51) Int. Cl.
*A01H 5/00* (2006.01)

(52) U.S. Cl. ..... Plt./373
(58) Field of Classification Search ..... Plt./373
See application file for complete search history.

*Primary Examiner*—Kent Bell
(74) *Attorney, Agent, or Firm*—C. A. Whealy

(57) ABSTRACT

A new and distinct cultivar of *Caladium* plant named 'White Marble', characterized by its upright and outwardly arching plant habit; vigorous growth habit; undulate strap-like leaves; and green and white-colored leaves.

3 Drawing Sheets

Botanical designation: *Caladium×hortulanum.*
Cultivar denomination: 'White Marble'.

BACKGROUND OF THE INVENTION

The present invention relates to a new and distinct cultivar of *Caladium* plant, botanically known as *Caladium× hortulanum,* commercially referred to as a strap-leaf *Caladium* and hereinafter referred to by the name 'White Marble'.

The new *Caladium* originated from a cross-pollination made by the Inventor in April, 2001, in Lake Placid, Fla. of the *Caladium×hortulanum* cultivar Grey Ghost, not patented, as the female, or seed, parent with the *Caladium× hortulanum* cultivar Lance Whorton, not patented, as the male, or pollen, parent. The new *Caladium* was discovered and selected by the Inventor as a single plant within the progeny of the stated cross-pollination in a controlled environment in Lake Placid, Fla. on Jun. 15, 2002.

Asexual reproduction of the new cultivar by tuber divisions in a controlled environment in Lake Placid, Fla. since Apr. 15, 2003 has shown that the unique features of this new *Caladium* are stable and reproduced true to type in successive generations of asexual reproduction.

SUMMARY OF THE INVENTION

The cultivar White Marble has not been observed under all possible environmental conditions. The phenotype may vary somewhat with variations in environment such as temperature and light intensity, without, however, any variance in genotype.

The following traits have been repeatedly observed and are determined to be the unique characteristics of 'White Marble'. These characteristics in combination distinguish 'White Marble' as a new and distinct cultivar of *Caladium:*

1. Upright and outwardly arching plant habit.
2. Vigorous growth habit.
3. Undulate strap-like leaves.
4. Green and white-colored leaves.

In side-by-side comparisons conducted in Lake Placid, Fla., plants of the new *Caladium* differed from plants of the female parent, the cultivar Grey Ghost, in the following characteristics:

1. Plants of the new *Caladium* were more compact than plants of the cultivar Grey Ghost.
2. Leaves of the plants of the new *Caladium* were strap-like whereas leaves of plants of the cultivar Grey Ghost were fancy types.
3. Leaves of plants of the new *Caladium* were more undulate than leaves of plants of the cultivar Grey Ghost.
4. Leaves of plants of the new *Caladium* were more rugose and more textured in appearance than leaves of plants of the cultivar Grey Ghost.
5. Plants of the new *Caladium* and the cultivar Grey Ghost differed in leaf coloration.

In side-by-side comparisons conducted in Lake Placid, Fla., plants of the new *Caladium* differed from plants of the male parent, the cultivar Lance Whorton, in the following characteristics:

1. Under high light conditions, plants of the new *Caladium* were taller than plants of the cultivar Lance Whorton.
2. Plants of the new *Caladium* and of the cultivar Lance Whorton differed in leaf coloration as plants of the cultivar Lance Whorton had pink-colored leaves with red-colored venation.

Plants of the new *Caladium* can also be compared to plants of the cultivar White Wing, not patented. In side-by-side comparisons conducted in Lake Placid, Fla., plants of the new *Caladium* differed from plants of the cultivar White Wing in the following characteristics:

1. Plants of the new *Caladium* were larger than plants of the cultivar White Wing.
2. Plants of the new *Caladium* and the cultivar White Wing differed in leaf coloration as plants of the cultivar White Wing had creamy white and green-colored leaves with pink to white-colored venation.
3. Plants of the new *Caladium* had longer leaf petioles than plants of the cultivar White Wing.

BRIEF DESCRIPTION OF THE PHOTOGRAPHS

The accompanying photographs illustrate the overall appearance of the new *Caladium.* These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet comprises a side perspective view of a typical plant of 'White Marble' grown in a container.

The photograph on the second sheet comprises a side perspective view of typical plants of 'White Marble' grown in a ground beds in an outdoor nursery.

The photograph at the top of the third sheet is a close-up view of a typical inflorescence of 'White Marble'.

The photograph at the bottom of the third sheet is a close-up view of typical tubers of 'White Marble'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in 15-cm containers in Lake Placid, Fla. during the spring in a polyethylene-covered shadehouse and under conditions and practices which approximate those generally used in commercial *Caladium* production. During the production of the plants, day temperatures ranged from about 21° C. to 38° C., night temperatures ranged from about 10° C. to 21° C. and light levels about 8,000 foot-candles. Plants were about seven weeks from planting tubers when the photographs and the detailed description were taken.

Botanical classification: *Caladium×hortulanum* cultivar White Marble.

Parentage:

*Female, or seed, parent.*—*Caladium×hortulanum* cultivar Grey Ghost, not patented.

*Male, or pollen, parent.*—*Caladium×hortulanum* cultivar Lance Whorton, not patented.

Propagation:

*Type.*—By tuber divisions.

*Time to initiate roots, summer.*—About seven to ten days at 32° C.

*Time to initiate roots, winter.*—About two to three weeks at 24° C.

*Tube description.*—Number of buds per tuber: About eight actively growing buds/shoots and about twelve dormant buds. Height: About 2.6 cm. Diameter: About 4.2 cm. Texture: Thick, starchy; somewhat brittle. Color: Epidermis, 200B; interior, 4D. Root description/habit: Dense, thick and white fleshy roots with finer lateral roots.

Plant description:

*Plant/growth habit.*—Upright and outwardly arching plant habit. Vigorous growth habit; suitable for 10-cm to 25-cm containers. Mostly upright leaf petioles.

*Plant height, from soil level to top of leaf plant.*—About 29 cm.

*Plant height, from soil level to top of inflorescences.*—About 39 cm.

*Plant spread.*—About 40 cm.

*Cataphylls.*—Length: About 7.5 cm. Width: About 1.8 cm. Shape: Linear to elliptic. Apex: Acuminate. Base: Sheathing the stem. Color, outer surface: 177D to 197C to 197D; streaks, N186B. Color, inner surface: 170D.

Foliage description:

*Length.*—About 12.9 cm.

*Width.*—About 10.1 cm.

*Shape.*—Ovate to lanceolate.

*Apex.*—Acuminate to acute.

*Base.*—Sagittate to cordate.

*Margin.*—Entire; undulate.

*Texture, upper surface.*—Smooth, glabrous; rugose giving a textured appearance.

*Texture, lower surface.*—Smooth, glabrous; glaucous; rugose giving a textured appearance.

*Venation pattern.*—Pinnate.

*Color.*—Developing leaves, upper surface: Margins: 147A to 147B. Center: Intervenal areas, 145D, often suffused with 137A; random white spots, N155A. Venation: Lateral veins, 193A; areas surrounding veins, 145D; veins at the petiole attachment, 155D, notch tinged with 59C; midrib, 193A to 193B. Developing leaves, lower surface: Margins: 191A. Center: Intervenal areas, 191C to 191D with random areas of 137B; random white spots, N155A. Venation: Laterals and midvein, 147C to 144C; areas surrounding veins, 155C; veins at the petiole attachment, 193A to 147C, notch tinged with 59C. Fully developed leaves, upper surface: Margins: 147A. Center: Intervenal areas, 193D, often suffused with 137A; random white spots, N155A to N155C. Venation: Lateral veins, 193A; areas surrounding veins, 193D; veins at the petiole attachment, 155C, notch, 60A; midrib, 193B. Fully developed leaves, lower surface: Margins: 191A. Center: Intervenal areas, 191C to 191D with random areas of 189A; random white spots, N155A. Venation: Laterals and midvein, 193A; areas surrounding veins, 193D; veins at the petiole attachment, 147C and 195B, notch, 60A to 183A.

*Petiole.*—Aspect: Mostly erect, outwardly arching with development. Length: About 23 cm. Diameter, distal: About 3.2 mm. Diameter, proximal: About 1.2 cm. Strength: Strong, flexible. Color: 177D and 147C; bars and streaks, N186A to N186B. Wing length: About 4.5 cm. Wing diameter: About 6 mm. Wing color, outer and inner surface: 147C to 177D; streaks, N186B.

Inflorescence description:

*Inflorescence arrangement.*—Hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this areas, the spathe constricts surrounding the female flowers.

*Fragrance.*—None detected.

*Natural flowering season/longevity.*—Plants of the new *Caladium* typically flower during the spring or early summer in central Florida. Flowers develop about eight to nine weeks after growth commences. Inflorescences last about three days before fading; inflorescences persistent.

*Spathe.*—Length: About 10.7 cm. Width: About 2.5 cm. Shape: Ovate. Apex: Acute. Base: Tapering. Margin: Entire. Texture, upper and lower surfaces:

Smooth, glabrous. Color: When developing, front surface: Upper two-thirds: 145D tinged with 155B. Lower one-third: 147B to 147C flushed with N77A. When developing, rear surface: Upper two-thirds: 145D. Lower one-third: 146A to 147B. Fully developed, front surface: Upper two-thirds: 145D tinged with 155A; with development, 199D tinged with 145D. Lower one-third: 147B to 147C flushed with N77A. Fully opened, rear surface: Upper two-thirds: 155A tinged with 145D; with development, 199D tinged with 145D. Lower one-third: 147B.

*Spadix.*—Length, entire spadix: About 7.4 cm. Length, male flower zone: About 5.3 cm. Length, sterile flower zone: About 1.2 cm. Length, female flower zone: About 9 mm. Diameter, male flower zone: About 9 mm. Diameter, sterile flower zone: About 6.7 mm. Diameter, female flower zone: About 7 mm. Shape: Columnar. Apex: Obtuse. Base: Obtuse. Aspect: Upright. Color: Immature, male zone: 8D tinged with 150C. Immature, female zone: 158D. Mature, male zone: 4D. Mature, female zone: 158B.

*Female flowers.*—Quantity per spadix: About 50. Shape: Ovate to elliptic. Height: About 2 mm. Diameter: About 2.5 mm. Stigma color: 8C. Ovary color: 158B.

*Male flowers.*—Quantity per spadix: About 84. Shape: Obovate; inverted triangle. Height: About 3.5 mm. Diameter: About 3 mm. Anther color: 4D. Amount of pollen: Moderate. Pollen color: 11C.

*Scape.*—Length: About 30 cm. Diameter: About 6 mm. Strength: Sturdy; flexible. Aspect: Erect. Texture: Smooth, glabrous; glaucous. Color: 177D and 147C; bars and streaks, N186A to N186B.

*Seed and fruit.*—Seed and fruit development has not been observed on plants of the new *Caladium.*

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'White Marble' as illustrated and described.

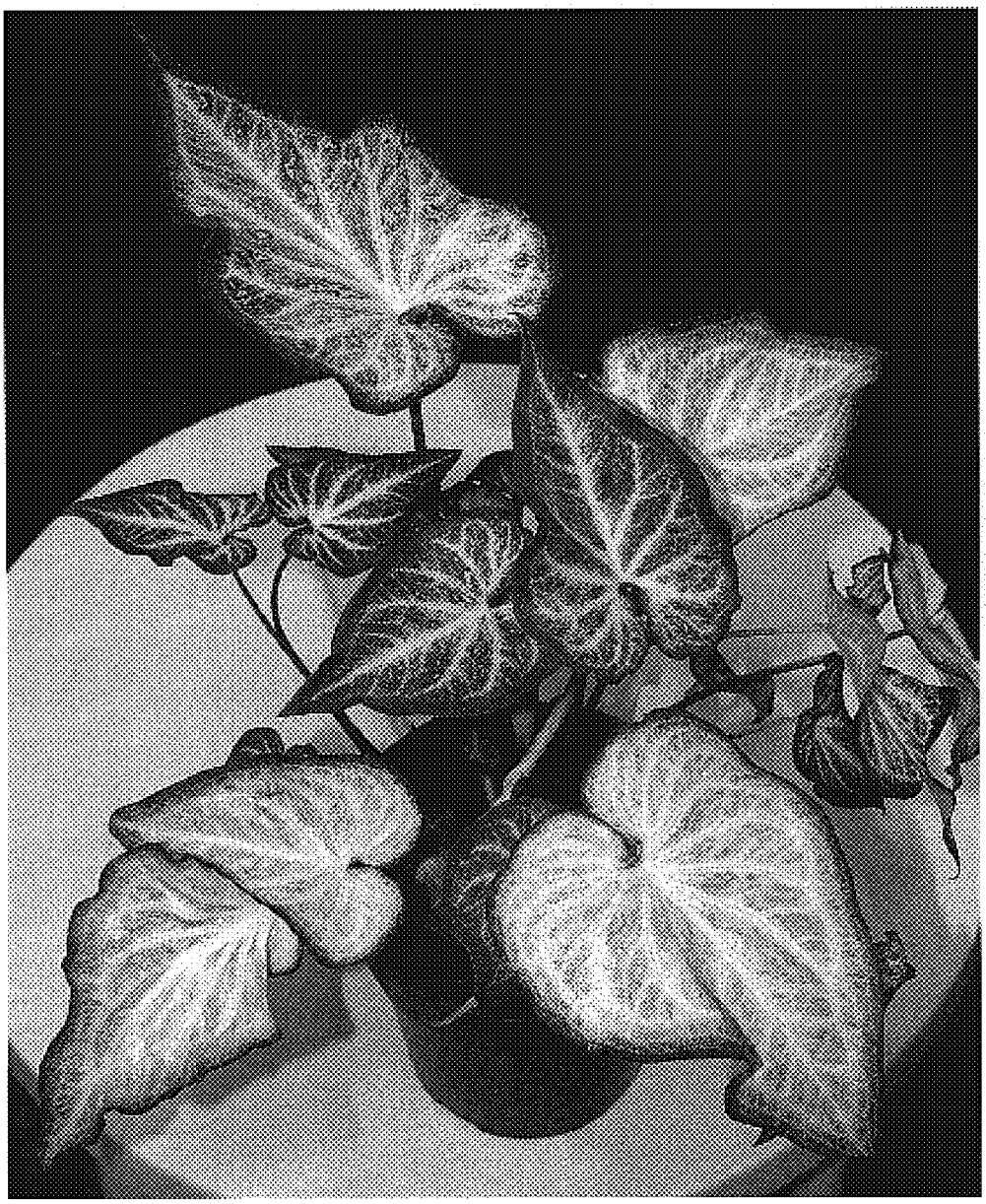

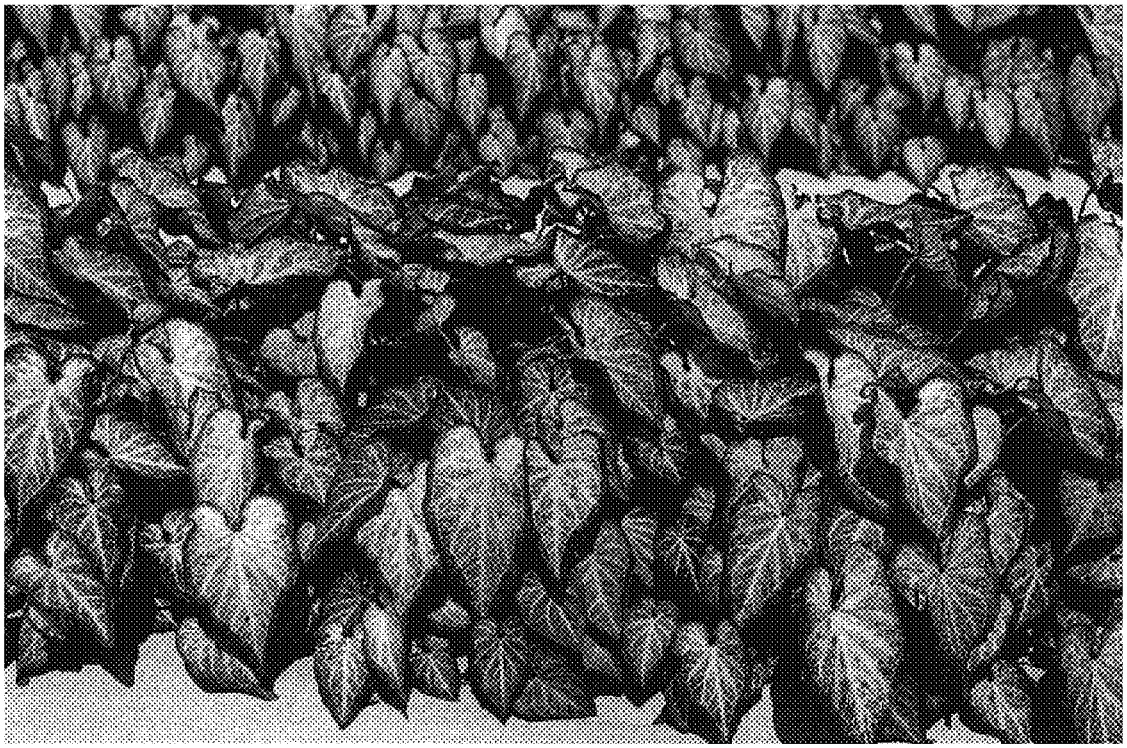

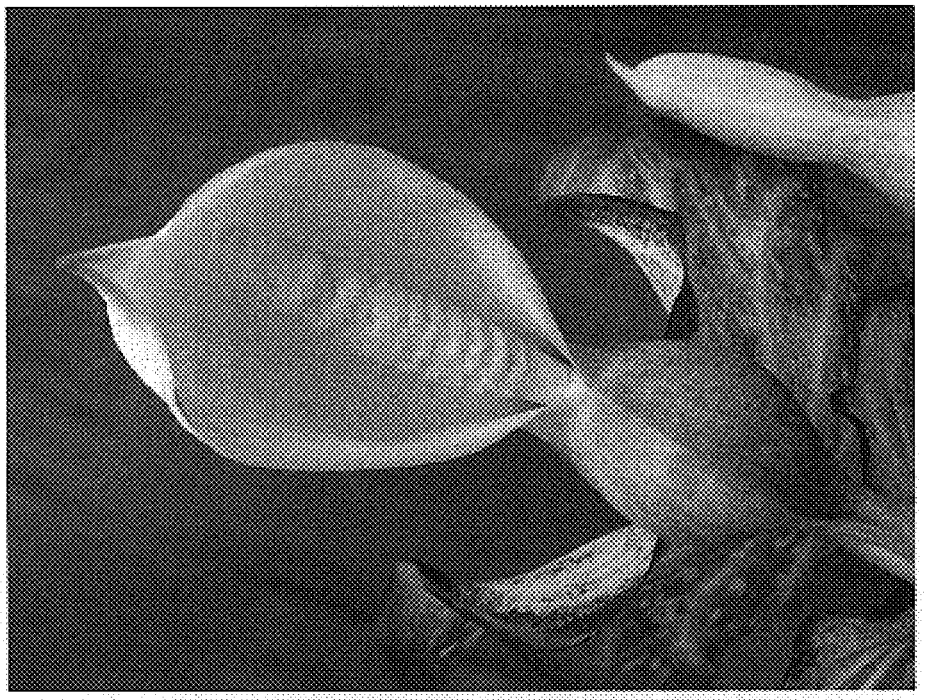
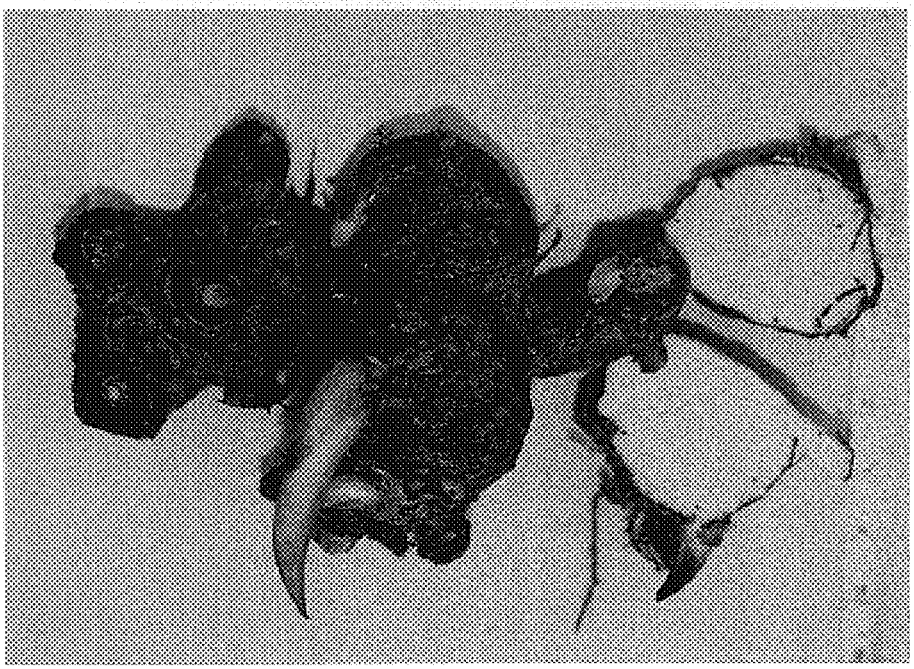

* * * * *